United States Patent
Zhou et al.

(10) Patent No.: US 10,800,852 B2
(45) Date of Patent: *Oct. 13, 2020

(54) ANTIBODY THERAPEUTICS THAT BIND CD38

(71) Applicant: Sorrento Therapeutics, Inc., San Diego, CA (US)

(72) Inventors: Heyue Zhou, San Diego, CA (US); John Dixon Gray, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 16/055,065

(22) Filed: Aug. 4, 2018

(65) Prior Publication Data

US 2019/0048092 A1 Feb. 14, 2019

Related U.S. Application Data

(63) Continuation of application No. 15/094,384, filed on Apr. 8, 2016, now Pat. No. 10,059,774.

(60) Provisional application No. 62/144,901, filed on Apr. 8, 2015.

(51) Int. Cl.
| | |
|---|---|
| *C07K 16/28* | (2006.01) |
| *C07K 16/40* | (2006.01) |
| *A61K 39/00* | (2006.01) |
| *A61K 39/395* | (2006.01) |

(52) U.S. Cl.
CPC .......... *C07K 16/2896* (2013.01); *A61K 39/00* (2013.01); *A61K 39/395* (2013.01); *A61K 39/39558* (2013.01); *C07K 16/40* (2013.01); *A61K 2039/505* (2013.01); *C07K 2317/21* (2013.01); *C07K 2317/56* (2013.01); *C07K 2317/565* (2013.01); *C07K 2317/72* (2013.01); *C07K 2317/732* (2013.01); *C07K 2317/92* (2013.01)

(58) Field of Classification Search
CPC ................ C07K 16/2896; C07K 16/40; C07K 2317/21; C07K 2317/56; C07K 2317/565; C07K 2317/72; C07K 2317/732; C07K 2317/92; A61K 39/00; A61K 39/395; A61K 39/39558; A61K 2039/505
See application file for complete search history.

(56) References Cited

U.S. PATENT DOCUMENTS

| 2003/0059937 A1 | 3/2003 | Ruben et al. | |
|---|---|---|---|
| 2013/0164309 A1* | 6/2013 | Quadros | C07K 16/30 424/174.1 |
| 2013/0171154 A1 | 7/2013 | Elias et al. | |
| 2017/0291959 A1 | 10/2017 | Gray et al. | |

FOREIGN PATENT DOCUMENTS

| WO | 2007042309 A2 | 4/2007 |
|---|---|---|
| WO | 2010054007 A1 | 5/2010 |
| WO | 2010141249 A2 | 12/2010 |
| WO | 2011154453 A1 | 12/2011 |

OTHER PUBLICATIONS

Paul, Fundamental Immunology, 3rd Edition, 1993, pp. 292-295.
Rudikoff et al., Proc. Natl. Acad. Sci. USA, 1982, 79(6):1979-1983.
Colman, Research in Immunology, 1994, 145:33-36.
Bendig, Methods: A Companion to Methods in Enzymology, 1995; 8:83-93.
Khantasup et al., Monoclonal Antibodies in Immunodiagnosis and Immunotherapy, 2015, 34(6): 404-417.
Kramer et al., "The human antibody repertoire specific for rabies virus glycoprotein as selected from immune libraries", European Journal of Immunology, 35(7):2131-2145, 2005.
Tian et al., "Immunodominance of the VH1-46 Antibody Gene Segment in the Primary Repertoire of Human Rotavirus-Specific B Cells is Reduced in the Memory Compartment through Somatic Mutation of Nondominant Clones", The Journal of Immunology,180(5):3279-3288, 2008.
International Search Report and Written Opinion for International Application No. PCT/US2016/026545 dated Jul. 26, 2016.
International Search Report and Written Opinion for International Application No. PCT/US2016/026567 dated Sep. 30, 2016.
International Preliminary Report on Patentability for PCT/US2016/026567, published Oct. 13, 2016, 8 pages.
International Preliminary Report on Patentability for PCT/US2016/026545, published Oct. 13, 2016, 4 pages.
Stevenson, G. "CD38 as a therapeutic target" Molecular Medi, Feinstein Inst. for Medical Research, vol. 12, No. 11-12, (2006).
European Patent Office, Supplementary Partial European Search Report relating to EP 16777327, completed Aug. 9, 2018, dated Aug. 20, 2018.
Deckert, J. et al. "SAR650984, A Novel Humanized CD38-Targeting Antibody, Demonstartes Potent Antitumor Activity in Models of Multiple Myeloma and other CD38+ Hematologic Malignancies", Clinical Cancer Research, vol. 20, No. 17 pp. 4574-4583, 2014.
European Patent Office, Extended European Search Report relating to EP 16777327, completed Aug. 9, 2018, dated Nov. 28, 2018.

* cited by examiner

Primary Examiner — Hong Sang
(74) Attorney, Agent, or Firm — McNeill Baur PLLC

(57) ABSTRACT

There is disclosed compositions and methods relating to or derived from anti-CD38 antibodies. More specifically, there is disclosed fully human antibodies that bind CD38, CD38-antibody binding fragments and derivatives of such antibodies, and CD38-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

20 Claims, 1 Drawing Sheet

Specification includes a Sequence Listing.

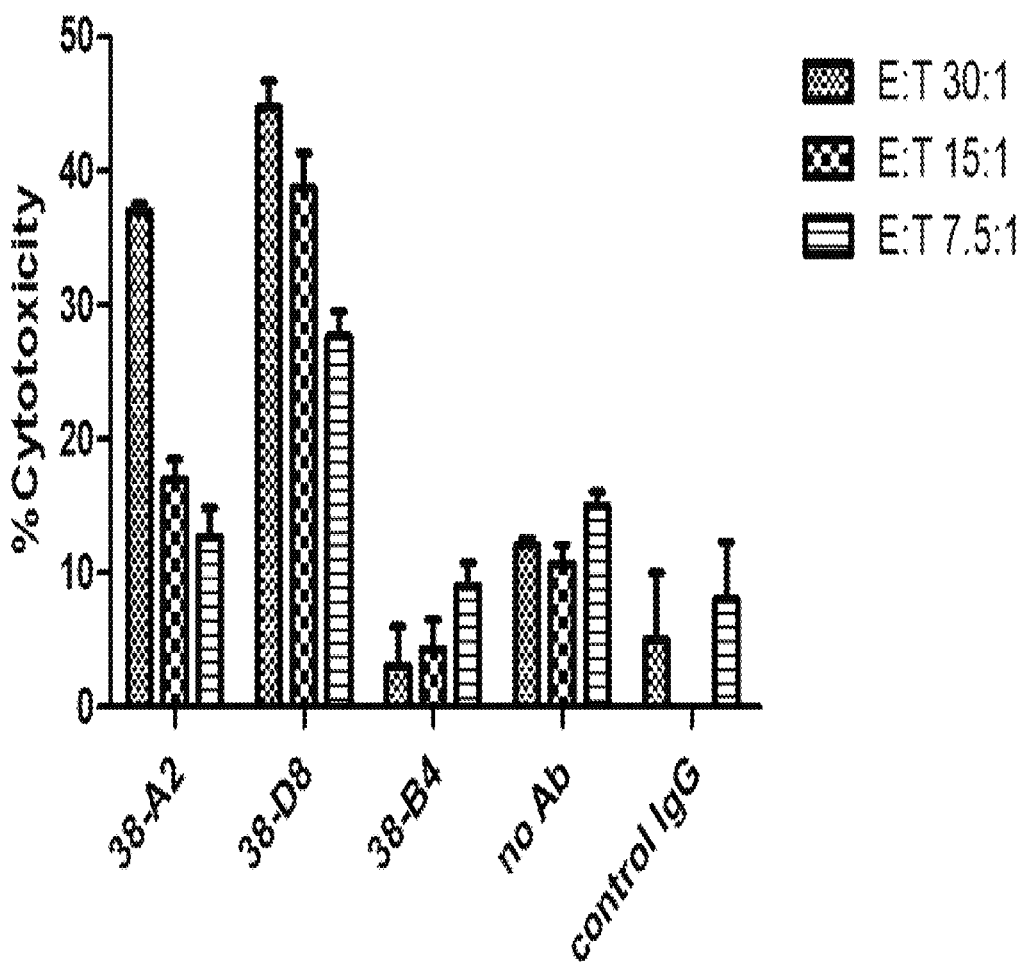

US 10,800,852 B2

ANTIBODY THERAPEUTICS THAT BIND CD38

RELATED APPLICATIONS

This application is a continuation of U.S. application Ser. No. 15/094,384, filed on Apr. 8, 2016, which claims priority to U.S. Provisional Application No. 62/144,901 filed on Apr. 8, 2015. The entire contents of these applications are explicitly incorporated herein by reference.

SEQUENCE LISTING

The instant application contains a Sequence Listing which has been submitted electronically in ASCII format and is hereby incorporated by reference in its entirety. Said ASCII copy, created on Oct. 30, 2018, is named S103014 1360USC1.TXT and is 34,689 bytes in size.

TECHNICAL FIELD

The present disclosure provides compositions and methods relating to or derived from anti-CD38 antibodies. More specifically, the present disclosure provides fully human antibodies that bind CD38, CD38-antibody binding fragments and derivatives of such antibodies, and CD38-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

BACKGROUND

CD38 is a 45 kD type II transmembrane glycoprotein with a long C-terminal extracellular domain and a short N-terminal cytoplasmic domain. The CD38 protein is a bifunctional ectoenzyme that can catalyze the conversion of NAD into cyclic ADP-ribose (cADPR) and also hydrolyze cADPR into ADP-ribose. During ontogeny, CD38 appears on $CD34^+$ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoeitic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are $CD38^-$. CD38 expression in hematopoietic malignancies and its correlation with disease progression makes CD38 an attractive target for anti-CD38 antibody therapy.

CD38 has been reported to be involved in $Ca^{2+}$ mobilization (Morra et al., 1998, FASEB J., 12: 581-592; Zilber et al., 2000, Proc Natl Acad Sci USA, 97: 2840-2845) and in the signal transduction through tyrosine phosphorylation of numerous signaling molecules, including phospholipase C-γ, ZAP-70, syk, and c-cbl, in lymphoid and myeloid cells or cell lines (Funaro et al., 1993, Eur J Immunol, 23: 2407-2411; Morra et al., 1998, FASEB J., 12: 581-592; Funaro et al., 1990, J Immunol, 145: 2390-2396; Zubiaur et al., 1997, J Immunol, 159: 193-205; Deaglio et al., 2003, Blood 102: 2146-2155; Todisco et al., 2000, Blood, 95: 535-542; Konopleva et al., 1998, J Immunol, 161: 4702-4708; Zilber et al., 2000, Proc Natl Acad Sci USA, 97: 2840-2845; Kitanaka et al., 1997, J Immunol, 159: 184-192; Kitanaka et al., 1999, J Immunol, 162: 1952-1958; Malone et al., 2001, Int Immunol, 13: 397-409). On the basis of these observations, CD38 was proposed to be an important signaling molecule in the maturation and activation of lymphoid and myeloid cells during their normal development.

The exact role of CD38 in signal transduction and hematopoiesis is still not clear, especially since most of these signal transduction studies have used cell lines ectopically overexpressing CD38 and anti-CD38 monoclonal antibodies, which are non-physiological ligands. Because the CD38 protein has an enzymatic activity that produces cADPR, a molecule that can induce $Ca^{2+}$ mobilization (Lee et al., 1989, J Biol Chem, 264:1608-1615; Lee and Aarhus, 1991, Cell Regul, 2: 203-209), it has been proposed that CD38 ligation by monoclonal antibodies triggers $Ca^{2+}$ mobilization and signal transduction in lymphocytes by increasing production of cADPR (Lee et al., 1997, Adv Exp Med Biol, 419: 411-419). Contrary to this hypothesis, the truncation and point-mutation analysis of CD38 protein showed that neither its cytoplasmic tail nor its enzymatic activity is necessary for the signaling mediated by anti-CD38 antibodies (Kitanaka et al., 1999, J Immunol, 162: 1952-1958; Lund et al., 1999, J Immunol, 162: 2693-2702; Hoshino et al., 1997, J Immunol, 158, 741-747).

Evidence for the function of CD38 comes from $CD38^{-/-}$ knockout mice, which have a defect in their innate immunity and a reduced T-cell dependent humoral response due to a defect in dendritic cell migration (Partida-Sanchez et al., 2004, Immunity, 20: 279-291; Partida-Sanchez et al., 2001, Nat Med, 7: 1209-1216). Nevertheless, it is not clear if the CD38 function in mice is identical to that in humans since the CD38 expression pattern during hematopoiesis differs greatly between human and mouse: a) unlike immature progenitor stem cells in humans, similar progenitor stem cells in mice express a high level of CD38 (Randall et al., 1996, Blood, 87: 4057-4067; Dagher et al., 1998, Biol Blood Marrow Transplant, 4: 69-74), b) while during the human B cell development, high levels of CD38 expression are found in germinal center B cells and plasma cells (Uckun, 1990, Blood, 76: 1908-1923; Kumagai et al., 1995, J Exp Med, 181: 1101-1110), in the mouse, the CD38 expression levels in the corresponding cells are low (Oliver et al., 1997, J Immunol, 158: 1108-1115; Ridderstad and Tarlinton 1998, J Immunol, 160: 4688-4695).

Several anti-human CD38 antibodies with different proliferative properties on various tumor cells and cell lines have been described in the literature. For example, a chimeric OKT10 antibody with mouse Fab and human IgG1 Fc mediates antibody-dependent cell-mediated cytotoxicity (ADCC) very efficiently against lymphoma cells in the presence of peripheral blood mononuclear effector cells from either MM patients or normal individuals (Stevenson et al., 1991, Blood, 77: 1071-1079). A CDR-grafted humanized version of the anti-CD38 antibody AT13/5 has been shown to have potent ADCC activity against CD38-positive cell lines. Human monoclonal anti-CD38 antibodies have been shown to mediate the in vitro killing of CD38-positive cell lines by ADCC and/or complement-dependent cytotoxicity (CDC), and to delay the tumor growth in SCID mice bearing MM cell line RPMI-8226 (WO2005/103083 A2). On the other hand, several anti-CD38 antibodies, IB4, SUN-4B7, and OKT10, but not IB6, AT1, or AT2, induced the proliferation of peripheral blood mononuclear cells (PBMC) from normal individuals (Ausiello et al. 2000, Tissue Antigens, 56: 539-547).

Some of the antibodies of the prior art have been shown to be able to trigger apoptosis in CD38$^+$ B cells. However, they can only do so in the presence of stroma cells or stroma-derived cytokines. An agonistic anti-CD38 antibody (IB4) has been reported to prevent apoptosis of human germinal center (GC) B cells (Zupo et al. 1994, Eur J Immunol, 24:1218-1222), and to induce proliferation of KG-1 and HL-60 AML cells (Konopleva et al. 1998, J Immunol, 161: 4702-4708), but induces apoptosis in Jurkat T lymphoblastic cells (Morra et al. 1998, FASEB J, 12: 581-592). Another anti-CD38 antibody T16 induced apoptosis of immature lymphoid cells and leukemic lymphoblast cells from an ALL patient (Kumagai et al. 1995, J Exp Med, 181: 1101-1110), and of leukemic myeloblast cells from AML patients (Todisco et al. 2000, Blood, 95: 535-542), but T16 induced apoptosis only in the presence of stroma cells or stroma-derived cytokines (IL-7, IL-3, stem cell factor).

SUMMARY

This invention pertains, at least in part, to proteins capable of binding to CD38, e.g., human CD38, including anti-CD38 antibodies, and antigen-binding fragments thereof.

In one aspect, the present disclosure provides an isolated fully human antibody of an IgG class that binds to a CD38 epitope, wherein said antibody comprises a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29, and a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, and SEQ ID NO. 20.

In one aspect, the present disclosure provides a fully human antibody of an IgG class that binds to a CD38 epitope with a binding affinity of at least $10^{-6}$M, which has a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and has a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

In one aspect, the present disclosure provides an isolated fully human anti-CD38 antibody comprising a heavy chain variable domain sequence as set forth in an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29; and comprising a light chain variable domain sequence as set forth in an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, and SEQ ID NO. 20.

In one embodiment, the fully human anti-CD38 antibody has both a heavy chain and a light chain wherein the antibody has a heavy chain/light chain variable domain sequence selected from the group consisting SEQ ID NO. 1/SEQ ID NO. 2 (called C38A1 herein), SEQ ID NO. 3/SEQ ID NO. 4 (called C38A2 herein), SEQ ID NO. 5/SEQ ID NO. 6 (called C38B1 herein), SEQ ID NO. 7/SEQ ID NO. 8 (called C38B4 herein), SEQ ID NO. 9/SEQ ID NO. 10 (called C38B7 herein), SEQ ID NO. 11/SEQ ID NO. 12 (called C38C4 herein), SEQ ID NO. 13/SEQ ID NO. 14 (called C38C9 herein), SEQ ID NO. 15/SEQ ID NO. 16 (called C38D1 herein), SEQ ID NO. 17/SEQ ID NO. 18 (called C38D2 herein), SEQ ID NO. 19/SEQ ID NO. 20 (called C38D5 herein), SEQ ID NO. 21/SEQ ID NO. 22 (called C38D8 herein), SEQ ID NO. 23/SEQ ID NO. 24 (called C38D10 herein), SEQ ID NO. 25/SEQ ID NO. 26 (called C38D11 herein), SEQ ID NO. 27/SEQ ID NO. 28 (called C38F8 herein), SEQ ID NO. 29/SEQ ID NO. 30 (called C38G8 herein), and combinations thereof.

In one embodiment, the present disclosure provides an anti-CD38 fully human antibody Fab fragment, having a variable domain region from a heavy chain and a variable domain region from a light chain, wherein the heavy chain variable domain comprises an amino acid sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and comprises a light chain variable domain comprising an amino acid sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof. In one embodiment, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof.

In one embodiment, the invention features a fully human antibody Fab fragment, comprising a heavy chain variable domain and a light chain variable domain, wherein the heavy chain variable domain comprises an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and the light chain variable domain comprises an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30.

In another aspect, the present disclosure provides an anti-CD38 single chain human antibody, having a variable domain region from a heavy chain and a variable domain region from a light chain and a peptide linker connecting the heavy chain and light chain variable domain regions, wherein the heavy chain variable domain comprises an amino acid sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and wherein the light chain variable domain comprises an amino acid sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

In one embodiment, the invention includes a fully human single chain antibody comprising both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof.

In another aspect, the present disclosure provides an anti-CD38 single chain human antibody, comprising a variable domain region from a heavy chain and a variable domain region from a light chain and a peptide linker connecting the heavy chain and light chain variable domain regions, wherein the heavy chain variable domain comprises an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and wherein the light chain variable domain comprises an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

Also included in the invention, is an isolated anti-CD38 antibody, or antigen-binding fragment thereof, comprising a heavy chain variable domain comprising complementarity determining regions (CDRs) as set forth in a heavy chain variable region amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29, and comprising a light chain variable region comprising CDRs as set forth in a light chain variable region amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30.

In one embodiment, the anti-CD38 fully human antibody or antibody fragment has a heavy chain variable domain that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and has a light chain variable domain comprising an amino acid sequence that is at least 95% identical, at least 96% identical, at least 97% identical, at least 98% identical, or at least 99% identical, to the amino acid consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof. In one embodiment, the fully human antibody, or antibody fragment, comprises a heavy chain variable domain comprising an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and comprises a light chain variable domain comprising an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

In certain embodiments, the anti-CD38 fully human antibody has both a heavy chain and a light chain wherein the antibody has a heavy chain/light chain variable domain sequence selected from the group consisting of SEQ ID NO. 1/SEQ ID NO. 2 (called C38A1 herein), SEQ ID NO. 3/SEQ ID NO. 4 (called C38A2 herein), SEQ ID NO. 5/SEQ ID NO. 6 (called C38B1 herein), SEQ ID NO. 7/SEQ ID NO.

8 (called C38B4 herein), SEQ ID NO. 9/SEQ ID NO. 10 (called C38B7 herein), SEQ ID NO. 11/SEQ ID NO. 12 (called C38C4 herein), SEQ ID NO. 13/SEQ ID NO. 14 (called C38C9 herein), SEQ ID NO. 15/SEQ ID NO. 16 (called C38D1 herein), SEQ ID NO. 17/SEQ ID NO. 18 (called C38D2 herein), SEQ ID NO. 19/SEQ ID NO. 20 (called C38D5 herein), SEQ ID NO. 21/SEQ ID NO. 22 (called C38D8 herein), SEQ ID NO. 23/SEQ ID NO. 24 (called C38D10 herein), SEQ ID NO. 25/SEQ ID NO. 26 (called C38D11 herein), SEQ ID NO. 27/SEQ ID NO. 28 (called C38F8 herein), SEQ ID NO. 29/SEQ ID NO. 30 (called C38G8 herein), and combinations thereof. In other embodiments, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof.

The present disclosure further provides a method for treating a broad spectrum of mammalian cancers, comprising administering an anti-CD38 polypeptide, e.g., an anti-human CD38 antibody, or antigen binding fragment thereof.

In certain embodiments, the broad spectrum of mammalian cancers to be treated is selected from the group consisting of non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

In certain embodiments, the anti-CD38 antibody, or antigen-binding fragment thereof, of the invention has a $K_D$ of at least $1 \times 10^{-6}$ M. In other embodiments, the anti-CD38 antibody, or antigen-binding fragment thereof, of the invention has a $K_D$ of at least $1 \times 10^{-7}$ M. In other embodiments, the anti-CD38 antibody, or antigen-binding fragment thereof, of the invention has a $K_D$ of at least $1 \times 10^{-8}$ M; at least $1 \times 10^{-9}$ M, or at least $1 \times 10^{-10}$ M.

In one embodiment, the anti-CD38 antibody is an IgG. In certain embodiments, the anti-CD38 antibody is an IgG1 isotype. In other embodiments, the anti-CD38 antibody is an IgG4 isotype.

In certain embodiments, the anti-CD38 antibody, or antigen-binding fragment, described herein is recombinant. In certain embodiments, the anti-CD38 antibody, or antigen-binding fragment, described herein is a human antibody, or antigen binding fragment of an antibody.

The invention also provides pharmaceutical compositions comprising an effective amount of an anti-CD38 antibodies or fragments disclosed herein, and a pharmaceutically acceptable carrier.

DESCRIPTION OF THE DRAWING

FIG. 1 is a graph that shows the results of an antibody-dependent cell-mediated cytotoxicity (ADCC) assay to assess the ability of anti-CD38 antibodies C38A2 ("38-A2"), C38D8 ("38-D8") and C38D4 ("38-D4") to bind to CD38 expressing cells and promote functional activity. Percent (%) cytotoxicity of each of the antibodies tested was determined. The data in FIG. 1 show that anti-CD38 antibodies 38-A2 and 38-D8 bound and promoted Antibody-Dependent Cell-Mediated Cytotoxicity (ADCC) activity against Ramos target cells. An IgG matched antibody was used as a control. The ADCC assay is performed by incubating natural killer cells (effector cells) with antibody coated tumor cells (target cells). The ratio of NK cells to tumor cells is referred to as the E:T ratio (effector to target ratio).

DETAILED DESCRIPTION

Definitions

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, a variant of an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et aL, 2003, Proteins: Structure, Function, and Bioinformatics, Volume 53, Issue 1:121-129; Roque et aL, 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of an immunoglobulin. An "immunoglobulin" is a tetrameric molecule, composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin or to an antigen binding portion thereof that competes with the intact antibody for specific binding, unless otherwise specified. In one embodiment, an antibody comprises two identical heavy chains each comprising a heavy chain variable domain (VH) and heavy chain constant regions $C_{H1}$, $C_{H2}$ and $C_{H3}$; and comprises two identical light chains each comprising a light chain variable domain (VL) and a light chain constant region ($C_L$). The heavy and light chain variable domain sequences may be selected from those described herein in SEQ ID Nos: 1 to 30.

In certain embodiments, antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific."

Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

In certain embodiments, an antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

An "antibody fragment" or "antigen binding fragment of an antibody" comprises a portion of an intact antibody, and preferably comprises the antibody antigen binding or variable domains. Examples of an antibody fragment include, but are not limited to, a Fab, an Fab', an F(ab')2, an Fv fragment, and a linear antibody. Antibody fragments are also referred to as "antibody portions" throughout.

Antigen binding portions (or fragments) of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the VL, VH, CL and CH1 domains; a F(ab')2 fragment is a bivalent fragment having two Fab fragments linked by a disulfide bridge at the hinge region; a Fd fragment has the VH and CH1 domains; an Fv fragment has the VL and VH domains of a single arm of an antibody; and a dAb fragment has a VH domain, a VL domain, or an antigen-binding fragment of a VH or VL domain (U.S. Pat. Nos. 6,846,634; 6,696,245, US App. Pub. 20/0202512; 2004/0202995; 2004/0038291; 2004/0009507; 20 03/0039958, and Ward et al., Nature 341:544-546, 1989).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., HoEiger et aL, 1993, Proc. Natl. Acad. Sci. USA 90:6444-48, and Poljak et aL, 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The term "human antibody" includes antibodies that have one or more variable and constant regions derived from human immunoglobulin sequences. In one embodiment, all of the variable and constant domains of the antibody are derived from human immunoglobulin sequences (referred to as "a fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods such that the glycosylation pattern of the antibody is different than an antibody having the same sequence if it were to exist in nature.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenic ity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CD38 antibody. In another embodiment, all of the CDRs are derived from a human anti-CD38 antibody. In another embodiment, the CDRs from more than one human anti-CD38 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-CD38 antibody, and the CDRs from the heavy chain from a third anti-CD38 antibody. Other combinations are possible.

Further, the framework regions may be derived from one of the same anti-CD38 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind CD38).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CD38) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or more than one expression vector) comprising the coding sequence of the antibody, or a portion thereof (e.g., a DNA sequence encoding a heavy chain or a light chain). In one embodiment, said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds CD38, which is sufficient to effect treatment of a disease when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the anti-CD38 antibodies, or antigen binding fragments, of the invention are isolated.

A "neutralizing antibody" or an "inhibitory antibody" is an antibody that inhibits the proteolytic activation of CD38 when an excess of the anti-CD38 antibody reduces the amount of activation by at least about 20% using an assay such as those described herein in the Examples. In various embodiments, the antigen binding protein reduces the amount of amount of proteolytic activation of CD38 by at least 30%, 40%, 50%, 60%, 70%, 75%, 80%, 85%, 90%, 95%, 97%, 99%, and 99.9%.

CD38 Antigen Binding Proteins

The present invention pertains to CD38 binding proteins, particularly anti-CD38 antibodies, or antigen-binding fragments thereof, (e.g., anti-CD38 human antibodies and antibody fragments) that bind CD38, e.g., human CD38, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human CD38, to inhibit CD38 activity, either in vitro or in vivo, and to prevent or treat disorders such as cancer are also encompassed by the invention.

As described in Table 1 below, included in the invention are novel antibody heavy and light chain variable regions that are specific to CD38. In one embodiment, the invention provides an anti-CD38 antibody, or an antigen-binding fragment thereof, that comprises a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29. In one embodiment, the invention provides an anti-CD38 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30. In one embodiment, the invention provides an anti-CD38 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30; and a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et aL, supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-CD38 antibody comprising the CDRs of a heavy and a light chain variable domain as described in Table 1 (SEQ ID Nos: 1 to 30). For example, the invention provides an anti-CD38 antibody, or antigen-binding fragment thereof, comprising a heavy chain variable region having CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29. In one embodiment, the invention provides an anti-CD38 antibody, or antigen-binding fragment thereof, comprising a light chain variable region having CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30. In one embodiment, the invention provides an anti-CD38 antibody, or antigen-binding fragment thereof, comprising a light chain variable region having CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, and SEQ ID NO. 20; and a heavy chain variable region having CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29.

In one embodiment, the present disclosure provides a fully human antibody of an IgG class that binds to a CD38 epitope with a binding affinity of at least $10^{-6}$M, which has a heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof. In one embodiment, the fully human antibody has both a heavy chain and a light chain wherein the antibody has a heavy chain/light chain variable domain sequence selected from the group consisting SEQ ID NO. 1/SEQ ID NO. 2 (called C38A1 herein), SEQ ID NO. 3/SEQ ID NO. 4 (called C38A2 herein), SEQ ID NO. 5/SEQ ID NO. 6 (called C38B1 herein), SEQ ID NO. 7/SEQ ID NO. 8 (called C38B4 herein), SEQ ID NO. 9/SEQ ID NO. 10 (called C38B7 herein), SEQ ID NO. 11/SEQ ID NO. 12 (called C38C4 herein), SEQ ID NO. 13/SEQ ID NO. 14 (called C38C9 herein), SEQ ID NO. 15/SEQ ID NO. 16 (called C38D1 herein), SEQ ID NO. 17/SEQ ID NO. 18 (called C38D2 herein), SEQ ID NO. 19/SEQ ID NO. 20 (called C38D5 herein), SEQ ID NO. 21/SEQ ID NO. 22 (called C38D8 herein), SEQ ID NO. 23/SEQ ID NO. 24 (called C38D10 herein), SEQ ID NO. 25/SEQ ID NO. 26 (called C38D11 herein), SEQ ID NO. 27/SEQ ID NO. 28 (called C38F8 herein), SEQ ID NO. 29/SEQ ID NO. 30 (called C38G8 herein), and combinations thereof.

In one embodiment, the invention provides an anti-CD38 antibody, or an antigen-binding fragment thereof, comprising a heavy chain comprising a CDR3 domain as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29, and comprising a variable domain comprising an amino acid sequence that has at least 95%, at least 96%, at least 97%, at least 98%, or at least 99% identical to a sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, and SEQ ID NO. 29. In one embodiment, the invention provides an anti-CD38 antibody, or an antigen-binding fragment thereof, comprising a light chain comprising a CDR3 domain as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30, and comprising a light chain variable domain comprising an amino acid sequence that has at least 95%, at least 96%, at least 97%, at least 98%, or at least 99% identical to a sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, and SEQ ID NO. 30. Thus, in certain embodiments, the CDR3 domain is held constant, while variability may be introduced into the remaining CDRs and/or framework regions of the heavy and/or light chain variable region sequences described herein, while the antibody, or antigen binding fragment thereof, retains the ability to bind to CD38 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 1. The antibodies of the invention, including those described in Table 1, bind to human CD38.

In one embodiment, the present invention is directed to an anti-CD38 antibody, or an antigen binding fragment thereof, having antigen binding regions of antibody C38A1. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 2. The antibody may further be an IgG1 or an IgG4 isotype.

In one embodiment, the present invention is directed to an anti-CD38 antibody, or an antigen binding fragment thereof, having antigen binding regions of antibody C38A2. In one embodiment, the invention provides an antibody, or antigen-binding fragment thereof, comprising a heavy chain variable domain sequence as set forth in SEQ ID NO: 3, and a light chain variable domain sequence as set forth in SEQ ID NO: 4. In one embodiment, the invention is directed to an antibody having a heavy chain variable domain comprising the CDRs of SEQ ID NO: 3, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 3, and comprises a light chain variable region having an amino acid sequence that is at least 95% identical, at least 96% identical, at least 97% identical, at least 98% identical, or at least 99% identical to the sequence set forth in SEQ ID NO: 4. The antibody may further be an IgG1 or an IgG4 isotype.

In one embodiment, the present invention is directed to an anti-CD38 antibody, or an antigen binding fragment thereof, having antigen binding regions of antibody C38B1. In one embodiment, the invention provides an antibody, or antigen-binding fragment thereof, comprising a heavy chain variable domain sequence as set forth in SEQ ID NO: 5, and a light chain variable domain sequence as set forth in SEQ ID NO: 6. In one embodiment, the invention is directed to an antibody having a heavy chain variable domain comprising the CDRs of SEQ ID NO: 5, and a light chain variable domain comprising the CDRs of SEQ ID NO: 6. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 5, and comprises a light chain variable region having an amino acid sequence that is at least 95% identical, at least 96% identical, at least 97% identical, at least 98% identical, or at least 99% identical to the sequence set forth in SEQ ID NO: 6. The antibody may further be an IgG1 or an IgG4 isotype.

In one embodiment, the present invention is directed to an anti-CD38 antibody, or an antigen binding fragment thereof, having antigen binding regions of antibody C38B4. In one embodiment, the invention provides an antibody, or antigen-binding fragment thereof, comprising a heavy chain variable domain sequence as set forth in SEQ ID NO: 7, and a light chain variable domain sequence as set forth in SEQ ID NO: 8. In one embodiment, the invention is directed to an antibody having a heavy chain variable domain comprising the CDRs of SEQ ID NO: 7, and a light chain variable domain comprising the CDRs of SEQ ID NO: 8. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 7, and comprises a light chain variable region having an amino acid sequence that is at least 95% identical, at least 96% identical, at least 97% identical, at least 98% identical, or at least 99% identical to the sequence set forth in SEQ ID NO: 8. The antibody may further be an IgG1 or an IgG4 isotype.

In one embodiment, the present invention is directed to an anti-CD38 antibody, or an antigen binding fragment thereof, having antigen binding regions of antibody C38B7. In one embodiment, the invention provides an antibody, or antigen-binding fragment thereof, comprising a heavy chain variable domain sequence as set forth in SEQ ID NO: 9, and a light chain variable domain sequence as set forth in SEQ ID NO: 10. In one embodiment, the invention is directed to an antibody having a heavy chain variable domain comprising the CDRs of SEQ ID NO: 9, and a light chain variable domain comprising the CDRs of SEQ ID NO: 10. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 9, and comprises a light chain variable region having an amino acid sequence that is at least 95% identical, at least 96% identical, at least 97% identical, at least 98% identical, or at least 99% identical to the sequence set forth in SEQ ID NO: 10. The antibody may further be an IgG1 or an IgG4 isotype.

In one embodiment, the present invention is directed to an anti-CD38 antibody, or an antigen binding fragment thereof, having antigen binding regions of antibody C38C4. In one embodiment, the invention provides an antibody, or antigen-binding fragment thereof, comprising a heavy chain variable domain sequence as set forth in SEQ ID NO: 11, and a light chain variable domain sequence as set forth in SEQ ID NO: 12. In one embodiment, the invention is directed to an antibody having a heavy chain variable domain comprising the CDRs of SEQ ID NO: 11, and a light chain variable domain comprising the CDRs of SEQ ID NO: 12. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 11, and comprises a light chain variable region having an amino acid sequence that is at least 95% identical, at least 96% identical, at least 97% identical, at least 98% identical, or at least 99% identical to the sequence set forth in SEQ ID NO: 12. The antibody may further be an IgG1 or an IgG4 isotype.

In one embodiment, the present invention is directed to an anti-CD38 antibody, or an antigen binding fragment thereof, having antigen binding regions of antibody C38C9. In one embodiment, the invention provides an antibody, or antigen-binding fragment thereof, comprising a heavy chain variable domain sequence as set forth in SEQ ID NO: 13, and a light chain variable domain sequence as set forth in SEQ ID NO: 14. In one embodiment, the invention is directed to an antibody having a heavy chain variable domain comprising the CDRs of SEQ ID NO: 13, and a light chain variable domain comprising the CDRs of SEQ ID NO: 14. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 13, and comprises a light chain variable region having an amino acid sequence that is at least 95% identical, at least 96% identical, at least 97% identical, at least 98% identical, or at least 99% identical to the sequence set forth in SEQ ID NO: 14. The antibody may further be an IgG1 or an IgG4 isotype.

In one embodiment, the present invention is directed to an anti-CD38 antibody, or an antigen binding fragment thereof, having antigen binding regions of antibody C38D1. In one embodiment, the invention provides an antibody, or antigen-binding fragment thereof, comprising a heavy chain variable domain sequence as set forth in SEQ ID NO: 15, and a light chain variable domain sequence as set forth in SEQ ID NO: 16. In one embodiment, the invention is directed to an antibody having a heavy chain variable domain comprising the CDRs of SEQ ID NO: 15, and a light chain variable domain comprising the CDRs of SEQ ID NO: 16. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 15, and comprises a light chain variable region having an amino acid sequence that is at least 95% identical, at least 96% identical, at least 97% identical, at least 98% identical, or at least 99% identical to the sequence set forth in SEQ ID NO: 16. The antibody may further be an IgG1 or an IgG4 isotype.

In one embodiment, the present invention is directed to an anti-CD38 antibody, or an antigen binding fragment thereof, having antigen binding regions of antibody C38D2. In one embodiment, the invention provides an antibody, or antigen-binding fragment thereof, comprising a heavy chain variable domain sequence as set forth in SEQ ID NO: 17, and a light chain variable domain sequence as set forth in SEQ ID NO: 18. In one embodiment, the invention is directed to an antibody having a heavy chain variable domain comprising the CDRs of SEQ ID NO: 17, and a light chain variable domain comprising the CDRs of SEQ ID NO: 18. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 17, and comprises a light chain variable region having an amino acid sequence that is at least 95% identical, at least 96% identical, at least 97% identical, at least 98% identical, or at least 99% identical to the sequence set forth in SEQ ID NO: 18. The antibody may further be an IgG1 or an IgG4 isotype.

In one embodiment, the present invention is directed to an anti-CD38 antibody, or an antigen binding fragment thereof, having antigen binding regions of antibody C38D5. In one embodiment, the invention provides an antibody, or antigen-binding fragment thereof, comprising a heavy chain variable domain sequence as set forth in SEQ ID NO: 19, and a light chain variable domain sequence as set forth in SEQ ID NO: 20. In one embodiment, the invention is directed to an antibody having a heavy chain variable domain comprising the CDRs of SEQ ID NO: 19, and a light chain variable domain comprising the CDRs of SEQ ID NO: 20. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 19, and comprises a light chain variable region having an amino acid sequence that is at least 95% identical, at least 96% identical, at least 97% identical, at least 98% identical, or at least 99% identical to the sequence set forth in SEQ ID NO: 20. The antibody may further be an IgG1 or an IgG4 isotype.

In one embodiment, the present invention is directed to an anti-CD38 antibody, or an antigen binding fragment thereof, having antigen binding regions of antibody C38D8. In one embodiment, the invention provides an antibody, or antigen-binding fragment thereof, comprising a heavy chain variable domain sequence as set forth in SEQ ID NO: 21, and a light chain variable domain sequence as set forth in SEQ ID NO: 22. In one embodiment, the invention is directed to an antibody having a heavy chain variable domain comprising the CDRs of SEQ ID NO: 21, and a light chain variable domain comprising the CDRs of SEQ ID NO: 22. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 21, and comprises a light chain variable region having an amino acid sequence that is at least 95% identical, at least 96% identical, at least 97% identical, at least 98% identical, or at least 99% identical to the sequence set forth in SEQ ID NO: 22. The antibody may further be an IgG1 or an IgG4 isotype.

In one embodiment, the present invention is directed to an anti-CD38 antibody, or an antigen binding fragment thereof, having antigen binding regions of antibody C38D10. In one embodiment, the invention provides an antibody, or antigen-binding fragment thereof, comprising a heavy chain variable domain sequence as set forth in SEQ ID NO: 23, and a light chain variable domain sequence as set forth in SEQ ID NO: 24. In one embodiment, the invention is directed to an antibody having a heavy chain variable domain comprising the CDRs of SEQ ID NO: 23, and a light chain variable domain comprising the CDRs of SEQ ID NO: 24. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 23, and comprises a light chain variable region having an amino acid sequence that is at least 95% identical, at least 96% identical, at least 97% identical, at least 98% identical, or at least 99% identical to the sequence set forth in SEQ ID NO: 24. The antibody may further be an IgG1 or an IgG4 isotype.

In one embodiment, the present invention is directed to an anti-CD38 antibody, or an antigen binding fragment thereof, having antigen binding regions of antibody C38D11. In one embodiment, the invention provides an antibody, or antigen-binding fragment thereof, comprising a heavy chain variable domain sequence as set forth in SEQ ID NO: 25, and a light chain variable domain sequence as set forth in SEQ ID NO: 26. In one embodiment, the invention is directed to an antibody having a heavy chain variable domain comprising the CDRs of SEQ ID NO: 25, and a light chain variable domain comprising the CDRs of SEQ ID NO: 26. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 25, and comprises a light chain variable region having an amino acid sequence that is at least 95% identical, at least 96% identical, at least 97% identical, at least 98% identical, or at least 99% identical to the sequence set forth in SEQ ID NO: 26. The antibody may further be an IgG1 or an IgG4 isotype.

In one embodiment, the present invention is directed to an anti-CD38 antibody, or an antigen binding fragment thereof, having antigen binding regions of antibody C38F8. In one embodiment, the invention provides an antibody, or antigen-binding fragment thereof, comprising a heavy chain variable domain sequence as set forth in SEQ ID NO: 27, and a light chain variable domain sequence as set forth in SEQ ID NO: 28. In one embodiment, the invention is directed to an antibody having a heavy chain variable domain comprising the CDRs of SEQ ID NO: 27, and a light chain variable domain comprising the CDRs of SEQ ID NO: 28. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 27, and comprises a light chain variable region having an amino acid sequence that is at least 95% identical, at least 96% identical, at least 97% identical, at least 98% identical, or at least 99% identical to the sequence set forth in SEQ ID NO: 28. The antibody may further be an IgG1 or an IgG4 isotype.

In one embodiment, the present invention is directed to an anti-CD38 antibody, or an antigen binding fragment thereof, having antigen binding regions of antibody C38G8. In one embodiment, the invention provides an antibody, or antigen-binding fragment thereof, comprising a heavy chain variable domain sequence as set forth in SEQ ID NO: 29, and a light chain variable domain sequence as set forth in SEQ ID NO: 30. In one embodiment, the invention is directed to an antibody having a heavy chain variable domain comprising the CDRs of SEQ ID NO: 29, and a light chain variable domain comprising the CDRs of SEQ ID NO: 30. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 29, and comprises a light chain variable region having an amino acid sequence that is at least 95% identical, at least 96% identical, at least 97% identical, at least 98% identical, or at least 99% identical to the sequence set forth in SEQ ID NO: 30. The antibody may further be an IgG1 or an IgG4 isotype.

Antigen-binding fragments of antigen binding proteins of the invention may be produced by conventional techniques. Examples of such fragments include, but are not limited to, Fab and F(ab')2 fragments.

In certain embodiment, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof. In certain embodiments, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof. In one embodiment, the present disclosure provides an anti-CD38 Fab fragment comprising a heavy chain variable domain comprising an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and a light chain variable domain comprising an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof. In certain embodiments, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof. In one embodiment, the present disclosure provides a single chain human antibody comprising a heavy chain variable domain and a light chain variable domain connected via a peptide linker, wherein the heavy chain variable domain comprises an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and the light chain variable domain comprises an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol. 178:303-16). Moreover, if an IgG4 is desired, it may also be desired to introduce a point mutation (CPSCP->CPPCP; SEQ ID NOS 31 and 32, respectively) in the hinge region (Bloom et al., 1997, Protein Science 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., Biochem. 32: 1180-1187 (1993); Kobayashi et al. Protein Eng. 12(10):879-884 (1999); and Burks et al. Proc. Natl. Acad. Sci. USA 94:412-417 (1997)). Near et al. Mol. Immunol. 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2). Thus, the invention also includes, in certain embodiments, variable sequences having at least 95% identity, at least 96% identity, at least 97% identity, at least 98% identity, or at least 99% identity to those sequences disclosed herein.

In certain embodiments, an antibody, or antigen-binding fragment thereof, provided herein has a dissociation constant ($K_D$) of $1 \times 10^{-6}$ M or less; $5 \times 10^{-7}$ M or less' $1 \times 10^{-7}$ M or less; $5 \times 10^{-8}$ M or less; $1 \times 10^{-8}$ M or less; $5 \times 10^{-9}$ M or less; or $1 \times 10^{-9}$ M or less. In one embodiment, the antibody, or antigen-binding fragment thereof, of the invention as a $K_D$ from $1 \times 10^{-7}$ M to $1 \times 10^{-10}$ M. In one embodiment, the antibody, or antigen-binding fragment thereof, of the invention as a $K_D$ from $1 \times 10^{-8}$ M to $1 \times 10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

In particular embodiments, antigen binding proteins of the present invention have a binding affinity ($K_a$) for CD38 of at least $10^6$ 1/Ms. In other embodiments, the antigen binding proteins exhibit a $K_a$ of at least $10^7$ 1/Ms, at least $10^8$ 1/Ms, at least $10^9$ 1/Ms, or at least $10^{10}$ 1/Ms. In another embodiment, the antigen binding protein exhibits a $K_a$ substantially the same as that of an antibody described herein in the Examples.

In another embodiment, the present disclosure provides an antigen binding protein that has a low dissociation rate from CD38. In one embodiment, the antigen binding protein has a $K_{off}$ of $1 \times 10^{-4}$ to $^{-1}$ $s^{-1}$ or lower. In another embodiment, the $K_{off}$ is $5 \times 10^{-5}$ to $^{-1}$ $s^{-1}$ or lower. In another embodiment, the $K_{off}$ is substantially the same as an antibody described herein. In another embodiment, the antigen binding protein binds to CD38 with substantially the same $K_{off}$ as an antibody described herein.

In another aspect, the present disclosure provides an antigen binding protein that inhibits an activity of CD38. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of CD38 with substantially the same IC$_{50}$ as an antibody described herein.

In another aspect, the present disclosure provides an antigen binding protein that binds to human CD38 expressed on the surface of a cell and, when so bound, inhibits CD38 signaling activity in the cell without causing a significant reduction in the amount of CD38 on the surface of the cell. Any method for determining or estimating the amount of CD38 on the surface and/or in the interior of the cell can be used. In other embodiments, binding of the antigen binding protein to the CD38-expressing cell causes less than about 75%, 50%, 40%, 30%, 20%, 15%, 10%, 5%, 1%, or 0.1% of the cell-surface CD38 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO2000/09560, incorporated by reference herein.

The present disclosure further provides multi-specific antigen binding proteins, for example, bispecific antigen binding protein, e.g., antigen binding protein that bind to two different epitopes of CD38, or to an epitope of CD38 and an epitope of another molecule, via two different antigen binding sites or regions. Moreover, bispecific antigen binding protein as disclosed herein can comprise a CD38 binding site from one of the herein-described antibodies and a second CD38 binding region from another of the herein-described antibodies, including those described herein by reference to other publications. Alternatively, a bispecific antigen binding protein may comprise an antigen binding site from one of the herein described antibodies and a second antigen binding site from another CD38 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, Nature 305:537, and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as CD38 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CD38 binding activity.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et aL, 1994, FEBS Letters 344:191. The use of a modified leucine zipper that allows for stable trimerization of a heterologous protein fused thereto is described in Fanslow et aL, 1994, Semin Immunol. 6:267-78. In one approach, recombinant fusion proteins comprising an anti-CD38 antibody fragment or derivative fused to a leucine zipper peptide are expressed in suitable host cells, and the soluble oligomeric anti-CD38 antibody fragments or derivatives that form are recovered from the culture supernatant.

Antigen binding proteins directed against CD38 can be used, for example, in assays to detect the presence of CD38 polypeptides, either in vitro or in vivo. The antigen binding proteins also may be employed in purifying CD38 proteins by immunoaffinity chromatography. Blocking antigen binding proteins can be used in the methods disclosed herein. Such antigen binding proteins that function as CD38 antagonists may be employed in treating any CD38-induced condition, including but not limited to various cancers.

Antigen binding proteins may be employed in an in vitro procedure, or administered in vivo to inhibit CD38-induced biological activity. Disorders that would benefit (directly or indirectly) from activation of CD38, examples of which are provided herein, thus may be treated. In one embodiment, the present invention provides a therapeutic method comprising in vivo administration of a CD38 blocking antigen binding protein to a mammal in need thereof in an amount effective for reducing a CD38-induced biological activity.

In certain embodiments, antigen binding proteins include fully human monoclonal antibodies that inhibit a biological activity of CD38.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CD38 bound thereto. Polypeptides contemplated for use herein include substantially homogeneous recombinant mammalian anti-CD38 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CD38 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression.

In one embodiment, the invention features nucleic acids encoding the antibodies or antibody fragments described herein. For example, in one embodiment, the invention includes a nucleic acid encoding a heavy chain variable domain as set forth in SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and encoding a light chain variable domain as set forth in SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

CD38-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to CD38. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen-binding fragments of antigen binding proteins of the invention may be produced by conventional techniques known in the art.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. Biochemistry. 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Methods, Formulations and Modes of Administration

The present disclosure further provides methods for treating a broad spectrum of mammalian cancers, comprising administering anti-CD38 antibodies or antigen binding fragments of the present invention.

In one embodiment, the present disclosure provides a method for treating cancer comprising administering an anti-CD38 antibody, or fragment thereof, selected from the group consisting of a fully human antibody of an IgG class that binds to a CD38 epitope with a binding affinity of at least $10^{-6}$M; a Fab fully human antibody fragment comprising a variable domain from a heavy chain and a variable domain from a light chain; a single chain human antibody, comprising a variable domain from a heavy chain and a variable domain from a light chain and a peptide linker connecting the heavy chain and light chain variable domains. The heavy and light chain variable regions (and CDRs within said sequences) that may be used in the antibodies and fragments of the invention are described in SEQ ID Nos. 1-30 (Table 1).

In one embodiment, the methods disclosed herein include the use of a fully human antibody comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and comprising a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof;

In one embodiment, the methods described herein include the use of a fully human Fab antibody fragment comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and that comprises a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

In one embodiment, the methods described herein include the use of a single chain human antibody comprising a heavy chain variable domain sequence that is at least 95% identical, at least 96% identical, at least 97% identical, at least 98% identical, or at least 99% identical, to an amino acid sequence selected from the group consisting of SEQ ID NO.

1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, and combinations thereof, and that comprises a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, and combinations thereof.

In one embodiment, the fully human antibody has both a heavy chain and a light chain wherein the antibody comprises a heavy chain/light chain variable domain sequence selected from the group consisting of SEQ ID NO. 1/SEQ ID NO. 2 (called C38A1 herein), SEQ ID NO. 3/SEQ ID NO. 4 (called C38A2 herein), SEQ ID NO. 5/SEQ ID NO. 6 (called C38B1 herein), SEQ ID NO. 7/SEQ ID NO. 8 (called C38B4 herein), SEQ ID NO. 9/SEQ ID NO. 10 (called C38B7 herein), SEQ ID NO. 11/SEQ ID NO. 12 (called C38C4 herein), SEQ ID NO. 13/SEQ ID NO. 14 (called C38C9 herein), SEQ ID NO. 15/SEQ ID NO. 16 (called C38D1 herein), SEQ ID NO. 17/SEQ ID NO. 18 (called C38D2 herein), SEQ ID NO. 19/SEQ ID NO. 20 (called C38D5 herein), SEQ ID NO. 21/SEQ ID NO. 22 (called C38D8 herein), SEQ ID NO. 23/SEQ ID NO. 24 (called C38D10 herein), SEQ ID NO. 25/SEQ ID NO. 26 (called C38D11 herein), SEQ ID NO. 27/SEQ ID NO. 28 (called C38F8 herein), SEQ ID NO. 29/SEQ ID NO. 30 (called C38G8 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called C38A1 herein), SEQ ID NO. 3/SEQ ID NO. 4 (called C38A2 herein), SEQ ID NO. 5/SEQ ID NO. 6 (called C38B1 herein), SEQ ID NO. 7/SEQ ID NO. 8 (called C38B4 herein), SEQ ID NO. 9/SEQ ID NO. 10 (called C38B7 herein), SEQ ID NO. 11/SEQ ID NO. 12 (called C38C4 herein), SEQ ID NO. 13/SEQ ID NO. 14 (called C38C9 herein), SEQ ID NO. 15/SEQ ID NO. 16 (called C38D1 herein), SEQ ID NO. 17/SEQ ID NO. 18 (called C38D2 herein), SEQ ID NO. 19/SEQ ID NO. 20 (called C38D5 herein), SEQ ID NO. 21/SEQ ID NO. 22 (called C38D8 herein), SEQ ID NO. 23/SEQ ID NO. 24 (called C38D10 herein), SEQ ID NO. 25/SEQ ID NO. 26 (called C38D11 herein), SEQ ID NO. 27/SEQ ID NO. 28 (called C38F8 herein), SEQ ID NO. 29/SEQ ID NO. 30 (called C38G8 herein), and combinations thereof.

In one embodiment, the fully human single chain antibody comprises both a heavy chain variable domain region and a light chain variable domain region, wherein the single chain fully human antibody comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, and combinations thereof.

The anti-CD38 antibodies and antibody fragments of the invention are used to treat a broad spectrum of mammalian cancers. In one embodiment, the cancer comprises any solid tumor or leukemic cell that expresses CD38 on the cell surface. In one embodiment, the cancer is selected from the group consisting of non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

In one embodiment, the anti-CD38 antibodies and antibody fragments of the invention are useful in treating, delaying the progression of, preventing relapse of or alleviating a symptom of a cancer or other neoplastic condition, including, hematological malignancies and/or CD38+ tumors. In one embodiment, the anti-CD38 antibodies and antibody fragments of the invention are useful in treating a cancer selected from the group consisting of non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and solid tumors, wherein solid tumors are selected from the group consisting of breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. It is understood that cases of leukemia are classified as acute or chronic.

Certain forms of leukemia include, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

In one embodiment, the present disclosure features methods for treating or preventing the S. aureus infection comprising administering anti-CD38 antibodies or antigen binding fragments of the present invention.

Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

In certain embodiments, the disclosed antibodies are administered by inhalation, but aerosolization of full IgG antibodies may prove limiting due to their molecular size (~150 kDa). To maximize available commercial aerosolization devices, smaller Fab fragments may be required.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 μg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

A CD38 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CD38 antibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to CD38. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CD38 protein is combined with the subject binding polypeptides, binding occurs between the binding polypeptides and the CD38 protein. In one embodiment, a sample containing cells expressing a CD38 protein (e.g., endothelial cells) is combined with the subject antibodies, and binding occurs between the binding polypeptides and cells bearing a CD38 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CD38 protein in a biological sample can also be prepared. Such kits will include a CD38 binding polypeptide which binds to a CD38 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

Having now described the present invention in detail, the same will be more clearly understood by reference to the following examples, which are included for purposes of illustration only and are not intended to be limiting of the invention.

Example

Human antibodies specific for human CD38 were identified and selected for therapeutic characteristics, including specificity for CD38 and a high degree of affinity for CD38 (e.g., at least $10^{-6}$ M). The identified antibodies are described in Table 1.

The ability of anti-CD38 antibodies to bind to CD38 expressing cells and promote functional activity was determined using an antibody-dependent cell-mediated cytotoxicity (ADCC) assay. In this assay, Ramos cells, a Burkitt's lymphoma cell line, were added to wells at $5 \times 10^3$ cells per well. Test antibodies (C38A2 ("38-A2"), C38D8 ("38-D8") and C38D4 ("38-D4") and control IgG) were then added at 1 microgram per ml and incubated with the Ramos cells for 20 minutes at 37° C. After washing, the effector cells were added at different concentrations resulting in three effector-to-target ratios. The effector cells were purified natural killer (NK) cells that had been incubated overnight in the presence of IL-2 (100 U/ml). The assay was allowed to proceed for at least 4 hours after which time cytotoxicity was evaluated using a Promega Cyto-glo kit.

The data in FIG. 1 show that anti-CD38 antibodies C38A2 and C38D8 bound and promoted ADCC activity against Ramos target cells.

TABLE 1

Amino Acid Sequences of Heavy and Light Chain Variable Domains

| | Heavy chain variable domain region | Light chain variable domain region |
|---|---|---|
| C38A1 | QVQLVESGAEVKKPGASVKVSCRAS GYTFTNYHLHWVRQAPGQGLEWVG TINPRGGSTTYAQKFQGRVAMTSDT STSTVYMEVNRLRSDDTAVYFCARG SDNALADFYNYYDMDVWGQGTTVT VSS SEQ ID NO. 1 | QAVVTQPPSVSAAPGQKVTISCSGSSSNIG NNYVSWYQQLPGTAPKLLIYDNNERPSGIP GRFSGSKSGTSATLGITGLQTGDEADYYC GTWDSSLSAGVFGGGTKLTVL SEQ ID NO. 2 |
| C38A2 | QVQLVESGGGLVKPGGSLRLSCAAS GFTFSDDYMSWIRQAPGKGLEWVAS VSNGRPTTYYADSVRGRFTISRDNAK NSLYLQMNSLRAEDTAVYYCARED WGGEFTDWGRGTLVTVSS SEQ ID NO. 3 | QAGLTQPPSASGTSGQRVTISCSGSSSNIGI NFVYWYQHLPGTAPKLLIYKNNQRPSGVP DRFSGSKSGNSASLAISGLRSEDEADYYCA AWDDSLSGYVFGSGTKVTVL SEQ ID NO. 4 |
| C38B1 | EVQLLESGAEVKKPGASVKVSCKAS GYTFTSYGISWVRQAPGQGLEWMG WISAYNGNTNYAQKLQGRVTMTTD TSTSTAYMELRSLRSDDTAVYYCAR TDLLYCSSTSCYHNGVGMDVWGQG TTVTVSS SEQ ID NO. 5 | QAVLTQPPSASGSPGQSVTISCTGTSSDVG GYNYVSWYQQHPDKAPKLIIYEVTKRPSG VPGRFSGSKSGNTASLTVSGLQAEDEADY YCGSYAGNNNYVFGTGTKVTVL SEQ ID NO. 6 |
| C38B4 | QVQLVESGAEVKKPGASVKVSCKAS GYTFTGYYMHWVRQAPGQGLEWM GWINPNSGGTNYAQKFQGRVTMTR DTSISTAYMELSRLSDDTAVYYCAR DPGGGDFDWGQGTLVTVSS SEQ ID NO. 7 | QPVLTQPASVSGSPGQSITISCTGTSSDVGG YNFVSWYQQHPGKAPKLMIYEGSKRPSGV PDRFSGSKSGNTASLTISGLQAEDEADYYC CSYAGSDTFVFGTGTKLTVL SEQ ID NO. 8 |

TABLE 1-continued

Amino Acid Sequences of Heavy and Light Chain Variable Domains

| | Heavy chain variable domain region | Light chain variable domain region |
|---|---|---|
| C38B7 | QVQLVQSGAEVKKPGSSVKVSCKSS GGTLRNYVINWVRQAPGQGLEWMG RITPFLGESESAQKFQNRVTITADTSI NTAYMELSSLRSEDTAVYYCARETV GATAADWYFDLWGRGTLVTVSS SEQ ID NO. 9 | QSVLTQPASVSGSPGQSITISCTGTSSDVGA YNYVSWYQQLPGAPKVLSYSNDHRPSG VPDRFSGSKSGTSASLAISGLQSEDEADYY CAAWDDSLNNYVFGTGTKVTVL SEQ ID NO. 10 |
| C38C4 | EVQLVQSGAEVKKPGASVKVSCKVS GYTLTELSMHWVRQAPGKGLEWMG GFDPEDGETIYAQKFQGRVTMTEDT STDTAYMELSSLRSEDTAVYYCATE NSNYVYFQHWGQGTLVTVSS SEQ ID NO. 11 | QSALTQPPSASGAPGQRVTISCSGSSANIGS NTVDWYQKLPGTAPRLLIYNDDHRPSGYP DRFSASTSGNTASLTIAGAQAEDEGDYYC NSRDNNDQHYVFGSGTKVTVL SEQ ID NO. 12 |
| C38C9 | EVQLVESGGGVVQPGRSLRLSCAAS GFTFSSYDMHWVRQATGKGLEWVS AIGTAGDTYYPGSVKGRFTISRDNSK NTLYLQMNSLRAEDTAVYYCARDS WFGELSLDWGQGTLVTVSS SEQ ID NO. 13 | QAVVTQAPSVSAAPGQKVTISCSGSSSNIG NNYVSWYQQLPGTAPKLLIYDNNKRPSGI PDRFSGSKSGTSATLGITGLQTGDEADYYC GTWDSSLSAAVFGGGTKLTVL SEQ ID NO. 14 |
| C38D1 | EVQLVQSGGGVVQPGRSLRVSCAAS GFTFSSYGMHWVRQTPGKGLEWVA GIWYDENDKYYADSVKGRFTISRDN SKNTLHLQMNSLRAEDTAVYYCAR QFRDYYFDVWGRGTLVTVSS SEQ ID NO. 15 | QSALTQPPSVSAAPGQKVTISCSGSSSNIGN NYVSWYQQLPGTAPKLLIYDNNKRPSGIP DRFSGSKSGTSATLGITGLQTGDEADYYC GTWDSSLGGVFGTGTKLTVL SEQ ID NO. 16 |
| C38D2 | QVQLVQSGSEVKKPGASLHLSCKAS GYTFINHYMHWVRQAPGQGLEWMG VINPRGGSTTYAQKFQGRVAMTTDT STYTVYMEVNSLRSDDTAVYFCARG SDNALADYYNSYDMDVWGQGTTVT VSS SEQ ID NO. 17 | AIRMTQSPSSLSASVGDRVTITCRASQGISS ALAWYQQKPGKAPKLLIYDASSLESGYPS RFSGSGSGTDFTLTISSLQPEDFATYYCQQ ANSFPLTFGQGTKLEIK SEQ ID NO. 18 |
| C38D5 | QVQLQQWGAGLLKPSETLSLTCAVY GGSFSGYYWSWIRQPPGKGLEWIGEI NHSGSTNYNPSLKSRVTISVDTSKNQ FSLKLSSVTAADTAVYYCAREGLRH SFDIWGQGTMVTVSS SEQ ID NO. 19 | QSVVTQPPSVSAAPGQKVTISCSGSNSNIGS NYVSWYQHLPGTAPKLLIYDNNNRPSGIP DRFSGSKSGTSATLGITGLQTGDEANYYC ATWDTSLSGWVFGGGTKLTVL SEQ ID NO. 20 |
| C38D8 | QVQLVESGGGVVQPGGSLRLSCAAS GFIVSTNYVHWVRQAPGKGLEWVS GIYSDPYTSYAYSDSVKGRFTISRDM SKNTVYLQMNRLRAEDTAVYYCAR ETNTGFSNSWYLDFWGQGTLVTVSS SEQ ID NO. 21 | QPVLTQPPSASGTPGQRVTISCSGSSSNIGR NIVNWYQQLPGTTPKLLIYSNNQRPSGVPD RFSGSKSGTSASLAISGLHSEDEADYYCAT WDDSLNGWVFGGGTKLTVL SEQ ID NO. 22 |
| C38D10 | QVQLVESGGGLVQPGGSLRLSCAAS GFTVSGNYMNWVRQAPGKGLEWVS VIYSGGDTYYADSVKGRFTVSRDNS KNTLYLQMNSLTAEDTAVYYCARE YSGYYYGMDVWGQGTTVTVSS SEQ ID NO. 23 | QSVLTQPHSASGTPGQRVTISCSGSSSNIGG NTVNWYQQLPGTAPRLLIYTNNKRPSGYP DRFSGSKSGTSASLAISGLQSEDEADYYCA AWDNSLKGYVFGTGTKLTVL SEQ ID NO. 24 |
| C38D11 | QVQLQQWGAGLLKPSETLSLTCAVY GGSFNGYYWSWIRQPPGKGLEWIGE INHSGSTNYNPSLKSRPTISVDTSKNQ FSLNLSSVTAADTAVYYCARAGTVY YYYGMDVWGQGTTVTVSS SEQ ID NO. 25 | QSVVTQPPSVSAAPGQKVTISCSGSNSNIA NNYVSWYQQLPGTAPKLLIYDNNKRPSGI PDRFSGSKSGTSATLGITGLQTGDEADYYC ETWDSSLSAVVFGGGTKLTVL SEQ ID NO. 26 |
| C38F8 | QVQLVQSGAEVKKPGESLEISCKDFG DSFTNWIGWVRQMPGKGLEWMGII YPGDSDTRYSPSFQGQVTISADKSINT AYLQWSSLKASDTAMYYCATFSREL MGFGAWGQGTLVTVSS SEQ ID NO. 27 | QSVLTQPPSVSATPGQRVTISCSGSSSNIGN NYVSWYQQLPGTAPKLLIYDNNKRPSGIP DRFSGSKSGTSAILDITGLQTGDEADYYCG TWDSSLSAEVFGTGTKLTVL SEQ ID NO. 28 |

TABLE 1-continued

Amino Acid Sequences of Heavy and Light Chain Variable Domains

| | Heavy chain variable domain region | Light chain variable domain region |
|---|---|---|
| C38G8 | EVQLLESGGGLVQPGRSLRLSCAASG FTFSSYGMHWVRQAPGKGLEWVSYI SSSSSTIYYADSVKGRFTISRDNAKNS LYLQMNSLRDEDTAVYYCARDEDY YYGMDVWGQGTTVTVSS SEQ ID NO. 29 | DIVMTQTPSSLSASVGDRVTITCQASQDIN GYLNWYQQKPGKAPKLLIYGASNLEKGV PSRFSGSGSGTDFTFTVSSLQSEDIATYYCQ QYDDLPLTFGAGTKVEIK SEQ ID NO. 30 |

We claim:

1. A pharmaceutical composition comprising an isolated, fully human antibody of an IgG class that binds to a CD38 epitope, wherein said antibody comprises
   (i) a heavy chain variable domain sequence comprising the amino acid sequence of SEQ ID NO: 3; and a light chain variable domain sequence comprising the amino acid sequence of SEQ ID NO: 4; or
   (ii) a heavy chain variable domain comprising CDR1, CDR2, and CDR3 of the amino acid sequence of SEQ ID NO: 3 and a light chain variable domain comprising CDR1, CDR2, and CDR3 of the amino acid sequence of SEQ ID NO: 4.

2. The pharmaceutical composition of claim 1, wherein said antibody comprises the heavy chain variable domain sequence comprising the amino acid sequence of SEQ ID NO: 3 and the light chain variable domain sequence comprising the amino acid sequence of SEQ ID NO: 4.

3. The pharmaceutical composition of claim 1, wherein the antibody is an IgG1 antibody.

4. The pharmaceutical composition of claim 1, wherein the antibody is an IgG4 antibody.

5. The pharmaceutical composition of claim 1, wherein the antibody is a full-length antibody.

6. The pharmaceutical composition of claim 1, wherein the antibody is an antibody fragment or single chain antibody comprising the heavy chain variable domain sequence and the light chain variable domain sequence.

7. The pharmaceutical composition of claim 6, wherein the antibody fragment or single chain antibody is a Fab or F(ab')$_2$ fragment or an scFv.

8. The pharmaceutical composition of claim 1, wherein the antibody is attached to another molecule.

9. The pharmaceutical composition of claim 8, wherein said another molecule is a label, enzyme, streptavidin, albumin, polyethylene glycol, transthyretin, or a transthyretin chemically modified with any one of dextran, poly(n-vinyl pyrrolidone), polyethylene glycol, a propylene glycol homopolymer, a polypropylene oxide/ethylene oxide co-polymer, a polyoxyethylated polyol, and a polyvinyl alcohol.

10. The pharmaceutical composition of claim 8, wherein said another molecule is a pharmaceutically active molecule.

11. The pharmaceutical composition of claim 8, wherein said another molecule is a polyethylene glycol.

12. The pharmaceutical composition of claim 1, wherein the antibody binds CD38 with a binding affinity of at least $10^{-6}$ M.

13. The pharmaceutical composition of claim 1, wherein the antibody binds CD38 with a binding affinity of at least $10^{-8}$ M.

14. The pharmaceutical composition of claim 2, wherein the antibody is an IgG1 antibody.

15. The pharmaceutical composition of claim 2, wherein the antibody is an antibody fragment or single chain antibody comprising the heavy chain variable domain sequence and the light chain variable domain sequence.

16. The pharmaceutical composition of claim 2, wherein the antibody is an IgG4 antibody.

17. The pharmaceutical composition of claim 2, wherein the antibody binds CD38 with a binding affinity of at least $10^{-6}$ M.

18. The pharmaceutical composition of claim 2, wherein the antibody binds CD38 with a binding affinity of at least $10^{-8}$ M.

19. The pharmaceutical composition of claim 8, wherein the antibody is an antibody fragment or single chain antibody comprising the heavy chain variable domain sequence and the light chain variable domain sequence.

20. Tale pharmaceutical composition of claim 1, comprising three heavy chain complementarity determining regions (CDRs) as set forth in the heavy chain variable region amino acid sequence of SEQ ID NO: 3 and three light chain CDRs as set forth in the light chain variable region amino acid sequence of SEQ ID NO: 4, wherein the antibody comprises a heavy chain variable domain comprising the amino acid sequence that is at least 95% identical to SEQ ID NO: 3 and a light chain variable domain comprising the amino acid sequence that is at least 95% identical to SEQ ID NO: 4.

* * * * *

SEQUENCE LISTING

```
<160> NUMBER OF SEQ ID NOS: 32

<210> SEQ ID NO 1
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Ala Glu Val Lys Lys Pro Gly Ala
1               5                   10                  15

Ser Val Lys Val Ser Cys Arg Ala Ser Gly Tyr Thr Phe Thr Asn Tyr
            20                  25                  30

His Leu His Trp Val Arg Gln Ala Pro Gly Gln Gly Leu Glu Trp Val
        35                  40                  45

Gly Thr Ile Asn Pro Arg Gly Gly Ser Thr Thr Tyr Ala Gln Lys Phe
    50                  55                  60

Gln Gly Arg Val Ala Met Thr Ser Asp Thr Ser Thr Ser Thr Val Tyr
65                  70                  75                  80

Met Glu Val Asn Arg Leu Arg Ser Asp Asp Thr Ala Val Tyr Phe Cys
                85                  90                  95

Ala Arg Gly Ser Asp Asn Ala Leu Ala Asp Phe Tyr Asn Tyr Tyr Asp
            100                 105                 110

Met Asp Val Trp Gly Gln Gly Thr Thr Val Thr Val Ser Ser
        115                 120                 125

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ala Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Gly Arg Phe Ser
    50                  55                  60

Gly Ser Lys Ser Gly Thr Ser Ala Thr Leu Gly Ile Thr Gly Leu Gln
65                  70                  75                  80
```

```
Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Gly Gly Phe Thr Asp Trp Gly Arg Gly Thr
            100                 105                 110

Leu Val Thr Val Ser Ser
        115

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ala Gly Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
            20                  25                  30

Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Ser Gly Thr Lys Val Thr Val Leu
            100                 105                 110

<210> SEQ ID NO 5
<211> LENGTH: 129
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 5

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Asp Leu Leu Tyr Cys Ser Ser Thr Ser Cys Tyr His Asn
                100                 105                 110

Gly Val Gly Met Asp Val Trp Gly Gln Gly Thr Thr Val Thr Val Ser
            115                 120                 125

Ser

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ala Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Ile Ile Tyr Glu Val Thr Lys Arg Pro Ser Gly Val Pro Gly Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Gly Ser Tyr Ala Gly Asn
                85                  90                  95

Asn Asn Tyr Val Phe Gly Thr Gly Thr Lys Val Thr Val Leu
                100                 105                 110

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
            20                  25                  30
Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Pro Gly Gly Gly Asp Phe Asp Tyr Trp Gly Gln Gly Thr
            100                 105                 110

Leu Val Thr Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Glu Gly Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Asp Thr Phe Val Phe Gly Thr Gly Thr Lys Leu Thr Val Leu
            100                 105                 110

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ser Gly Gly Thr Leu Arg Asn Tyr
            20                  25                  30

Val Ile Asn Trp Val Arg Gln Ala Pro Gly Gln Gly Leu Glu Trp Met
        35                  40                  45

Gly Arg Ile Thr Pro Phe Leu Gly Glu Ser Glu Ser Ala Gln Lys Phe
    50                  55                  60

Gln Asn Arg Val Thr Ile Thr Ala Asp Thr Ser Ile Asn Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Glu Thr Val Gly Ala Thr Ala Ala Asp Trp Tyr Phe Asp Leu
                100                 105                 110

Trp Gly Arg Gly Thr Leu Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
                20                  25                  30

Asn Tyr Val Ser Trp Tyr Gln Gln Leu Pro Gly Thr Ala Pro Lys Val
            35                  40                  45

Leu Ser Tyr Ser Asn Asp His Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Ser Ser
                85                  90                  95

Leu Asn Asn Tyr Val Phe Gly Thr Gly Thr Lys Val Thr Val Leu
            100                 105                 110

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Asn Ser Asn Tyr Val Tyr Phe Gln His Trp Gly Gln Gly
            100                 105                 110

Thr Leu Val Thr Val Ser Ser
        115

<210> SEQ ID NO 12
<211> LENGTH: 110
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 12

Gln Ser Ala Leu Thr Gln Pro Pro Ser Ala Ser Gly Ala Pro Gly Gln
1               5                   10                  15

Arg Val Thr Ile Ser Cys Ser Gly Ser Ser Ala Asn Ile Gly Ser Asn
            20                  25                  30

Thr Val Asp Trp Tyr Gln Lys Leu Pro Gly Thr Ala Pro Arg Leu Leu
        35                  40                  45

Ile Tyr Asn Asp Asp His Arg Pro Ser Gly Val Pro Asp Arg Phe Ser
50                  55                  60

Ala Ser Thr Ser Gly Asn Thr Ala Ser Leu Thr Ile Ala Gly Ala Gln
65                  70                  75                  80

Ala Glu Asp Glu Gly Asp Tyr Tyr Cys Asn Ser Arg Asp Asn Asn Asp
                85                  90                  95

Gln His Tyr Val Phe Gly Ser Gly Thr Lys Val Thr Val Leu
            100                 105                 110

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Trp Phe Gly Glu Leu Ser Leu Asp Tyr Trp Gly Gln Gly
            100                 105                 110

Thr Leu Val Thr Val Ser Ser
        115

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ala Val Val Thr Gln Ala Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30
```

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Ala Val Phe Gly Gly Gly Thr Lys Leu Thr Val Leu
            100                 105                 110

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Gly Met His Trp Val Arg Gln Thr Pro Gly Lys Gly Leu Glu Trp Val
        35                  40                  45

Ala Gly Ile Trp Tyr Asp Glu Asn Asp Lys Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Arg Gln Phe Arg Asp Tyr Tyr Phe Asp Val Trp Gly Arg Gly Thr
            100                 105                 110

Leu Val Thr Val Ser Ser
        115

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Ala Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

-continued

Gly Gly Val Phe Gly Thr Gly Thr Lys Leu Thr Val Leu
            100                 105

<210> SEQ ID NO 17
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ser Glu Val Lys Lys Pro Gly Ala
1               5                   10                  15

Ser Leu His Leu Ser Cys Lys Ala Ser Gly Tyr Thr Phe Ile Asn His
            20                  25                  30

Tyr Met His Trp Val Arg Gln Ala Pro Gly Gln Gly Leu Glu Trp Met
        35                  40                  45

Gly Val Ile Asn Pro Arg Gly Ser Thr Thr Tyr Ala Gln Lys Phe
    50                  55                  60

Gln Gly Arg Val Ala Met Thr Thr Asp Thr Ser Thr Tyr Thr Val Tyr
65                  70                  75                  80

Met Glu Val Asn Ser Leu Arg Ser Asp Thr Ala Val Tyr Phe Cys
                85                  90                  95

Ala Arg Gly Ser Asp Asn Ala Leu Ala Asp Tyr Tyr Asn Ser Tyr Asp
            100                 105                 110

Met Asp Val Trp Gly Gln Gly Thr Thr Val Thr Val Ser Ser
        115                 120                 125

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gln Gly Thr Lys Leu Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Leu Arg His Ser Phe Asp Ile Trp Gly Gln Gly Thr Met
            100                 105                 110

Val Thr Val Ser Ser
            115

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Ser Asn
            20                  25                  30

Tyr Val Ser Trp Tyr Gln His Leu Pro Gly Thr Ala Pro Lys Leu Leu
        35                  40                  45

Ile Tyr Asp Asn Asn Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Thr Ser Leu
                85                  90                  95

Ser Gly Trp Val Phe Gly Gly Gly Thr Lys Leu Thr Val Leu
            100                 105                 110

<210> SEQ ID NO 21
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Val Ser Thr Asn
            20                  25                  30

Tyr Val His Trp Val Arg Gln Ala Pro Gly Lys Gly Leu Glu Trp Val
        35                  40                  45

```
Ser Gly Ile Tyr Ser Asp Pro Tyr Thr Ser Tyr Ala Tyr Ser Asp Ser
        50                  55                  60

Val Lys Gly Arg Phe Thr Ile Ser Arg Asp Met Ser Lys Asn Thr Val
 65                  70                  75                  80

Tyr Leu Gln Met Asn Arg Leu Arg Ala Glu Asp Thr Ala Val Tyr Tyr
                85                  90                  95

Cys Ala Arg Glu Thr Asn Thr Gly Phe Ser Asn Ser Trp Tyr Leu Asp
                100                 105                 110

Phe Trp Gly Gln Gly Thr Leu Val Thr Val Ser Ser
            115                 120
```

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Pro Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Arg Asn
                20                  25                  30

Ile Val Asn Trp Tyr Gln Gln Leu Pro Gly Thr Thr Pro Lys Leu Leu
                35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu His
 65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
                100                 105                 110
```

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Gly Asn
                20                  25                  30

Tyr Met Asn Trp Val Arg Gln Ala Pro Gly Lys Gly Leu Glu Trp Val
                35                  40                  45

Ser Val Ile Tyr Ser Gly Gly Asp Thr Tyr Tyr Ala Asp Ser Val Lys
        50                  55                  60

Gly Arg Phe Thr Val Ser Arg Asp Asn Ser Lys Asn Thr Leu Tyr Leu
 65                  70                  75                  80

Gln Met Asn Ser Leu Thr Ala Glu Asp Thr Ala Val Tyr Tyr Cys Ala
                85                  90                  95

Arg Glu Tyr Ser Gly Tyr Tyr Tyr Gly Met Asp Val Trp Gly Gln Gly
                100                 105                 110
```

```
Thr Thr Val Thr Val Ser Ser
        115

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ser Val Leu Thr Gln Pro His Ser Ala Gly Thr Pro Gly Gln
1               5                   10                  15

Arg Val Thr Ile Ser Cys Ser Gly Ser Ser Asn Ile Gly Gly Asn
                20                  25                  30

Thr Val Asn Trp Tyr Gln Gln Leu Pro Gly Thr Ala Pro Arg Leu Leu
            35                  40                  45

Ile Tyr Thr Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asn Ser Leu
                85                  90                  95

Lys Gly Tyr Val Phe Gly Thr Gly Thr Lys Leu Thr Val Leu
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Asn Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Pro Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Ala Gly Thr Val Tyr Tyr Tyr Gly Met Asp Val Trp Gly Gln
            100                 105                 110

Gly Thr Thr Val Thr Val Ser Ser
        115                 120

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 26

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Ala Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Ser Ala Val Val Phe Gly Gly Gly Thr Lys Leu Thr Val Leu
            100                 105                 110

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Glu
1               5                   10                  15

Ser Leu Glu Ile Ser Cys Lys Asp Phe Gly Asp Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Thr Phe Ser Arg Glu Leu Met Gly Phe Gly Ala Trp Gly Gln Gly
            100                 105                 110

Thr Leu Val Thr Val Ser Ser
        115

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ser Val Leu Thr Gln Pro Pro Ser Val Ser Ala Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
```

```
            50                  55                  60
Gly Ser Lys Ser Gly Thr Ser Ala Ile Leu Asp Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Glu Val Phe Gly Thr Gly Thr Lys Leu Thr Val Leu
                100                 105                 110

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Asp Glu Asp Tyr Tyr Tyr Gly Met Asp Val Trp Gly Gln Gly
                100                 105                 110

Thr Thr Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Thr Pro Ser Ser Leu Ser Ala Ser Val Gly
 1               5                  10                  15

Asp Arg Val Thr Ile Thr Cys Gln Ala Ser Gln Asp Ile Asn Gly Tyr
                20                  25                  30

Leu Asn Trp Tyr Gln Gln Lys Pro Gly Lys Ala Pro Lys Leu Leu Ile
            35                  40                  45

Tyr Gly Ala Ser Asn Leu Glu Lys Gly Val Pro Ser Arg Phe Ser Gly
 50                  55                  60

Ser Gly Ser Gly Thr Asp Phe Thr Phe Thr Val Ser Ser Leu Gln Ser
 65                  70                  75                  80

Glu Asp Ile Ala Thr Tyr Tyr Cys Gln Gln Tyr Asp Asp Leu Pro Leu
                85                  90                  95

Thr Phe Gly Ala Gly Thr Lys Val Glu Ile Lys
                100                 105
```

```
<210> SEQ ID NO 31
<211> LENGTH: 5
<212> TYPE: PRT
<213> ORGANISM: Unknown
<220> FEATURE:
<223> OTHER INFORMATION: Description of Unknown: Hinge region
      peptide

<400> SEQUENCE: 31

Cys Pro Ser Cys Pro
1               5

<210> SEQ ID NO 32
<211> LENGTH: 5
<212> TYPE: PRT
<213> ORGANISM: Unknown
<220> FEATURE:
<223> OTHER INFORMATION: Description of Unknown: Hinge region
      peptide

<400> SEQUENCE: 32

Cys Pro Pro Cys Pro
1               5
```